(12) United States Patent
Rauleder et al.

(10) Patent No.: US 9,474,692 B2
(45) Date of Patent: Oct. 25, 2016

(54) KIT FOR THE PREPARATION OF A VACCINATING AGENT

(71) Applicant: Boehringer Ingelheim Vetmedica GmbH, Ingelheim am Rhein (DE)

(72) Inventors: Dirk Neven Rauleder, Ingelheim am Rhein (DE); Gerald Behrens, Engelstadt (DE); Knut Elbers, Mittelbiberach (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 124 days.

(21) Appl. No.: 13/740,740

(22) Filed: Jan. 14, 2013

(65) Prior Publication Data

US 2013/0183337 A1  Jul. 18, 2013

Related U.S. Application Data

(60) Provisional application No. 61/586,353, filed on Jan. 13, 2012.

(51) Int. Cl.
| | | |
|---|---|---|
| *A61J 3/00* | (2006.01) | |
| *A61J 1/20* | (2006.01) | |
| *A61D 1/02* | (2006.01) | |
| *A61D 7/00* | (2006.01) | |

(52) U.S. Cl.
CPC ............... *A61J 3/00* (2013.01); *A61D 1/025* (2013.01); *A61J 1/2089* (2013.01); *A61D 7/00* (2013.01); *A61J 1/201* (2015.05); *A61J 1/2013* (2015.05)

(58) Field of Classification Search
CPC .. A61J 3/00; A61J 2001/2013; A61J 1/2089; A61D 7/00; A61D 1/025
See application file for complete search history.

(56) References Cited

U.S. PATENT DOCUMENTS

| | | | |
|---|---|---|---|
| 4,405,047 A * | 9/1983 | Barba | 206/570 |
| 5,466,220 A | 11/1995 | Brenneman | |
| 5,637,087 A * | 6/1997 | O'Neil et al. | 604/82 |
| 6,335,200 B1 * | 1/2002 | Tiru et al. | 436/7 |
| 7,135,180 B2 * | 11/2006 | Truong-Le | 424/184.1 |
| 2003/0017171 A1 * | 1/2003 | Chu et al. | 424/201.1 |

FOREIGN PATENT DOCUMENTS

| | | |
|---|---|---|
| EP | 1 829 518 A1 | 9/2007 |
| WO | 2006/072065 A2 | 7/2006 |
| WO | WO 2009127684 A1 * | 10/2009 |

OTHER PUBLICATIONS

Anonymous: Vista 3 VL SQ, Bovine Rhinotracheitis—Virus Diarrhea Vaccine, Modified Live Virus—Campylobacter Fetus—Leptospira Canicola—Grippotyphosa—Hardjo—Icterohaemorrhagiae—Pomona Bacterin, Jan. 1, 2009, Found on the Internet, URL: http://www.merck-animal-health-usa.com/products/vista3v15sq/overview.aspx, e.g. point 3 on p. 3, the whole document.

Anonymous: Summary of Product Characteristics, Jan. 1, 2008, Found on the Internet, URL: http://www.ema.europa.eu/docs/en_GB/document_library/EPAR - Product_Information/human/000832/WC500038121.pdf, found on May 7, 2013.

* cited by examiner

*Primary Examiner* — Stacy B Chen
(74) *Attorney, Agent, or Firm* — David S. Safran

(57) ABSTRACT

A kit, a method of using it and a process for preparing a vaccine for immunization against the disease Porcine Circovirus Disease and/or Enzootic Pneumonia in pigs are proposed, in which a first container is only partly filled with a first vaccine and a second container is filled with a second vaccine, the second vaccine being transferred into the first container through an adapter device, when a closure device is penetrated for the first and/or only time, and the vaccinating agent is prepared therein, thus making the operation simple, less error-prone and more hygienic, while reducing the materials required. The adapter device has a pair of oppositely facing piercing elements formed of one of needles, hollow, spikes, wedges with at least one through passage extending through both piercing elements, each of the containers being pierced by a respective one of the piercing elements creating a fluid connection between the containers.

15 Claims, 4 Drawing Sheets

US 9,474,692 B2

KIT FOR THE PREPARATION OF A VACCINATING AGENT

BACKGROUND OF THE INVENTION

1. Field of the Invention

The present invention relates to a kit for the preparation of a vaccinating agent, a process for preparing a vaccinating agent by means of such a kit, a use of at least two starting materials for preparing a vaccinating agent and a process for providing or producing a vaccinating agent.

The present invention relates in particular to the manufacture and provision of vaccinating agents, particularly in the veterinary medical field. Primarily, the present invention relates to vaccinating agents for immunizing pigs against Porcine Circovirus, particularly type 2, also known as Porcine Circovirus Disease or PCVD, and/or against bacteria of the strain *Mycoplasma hyopneumoniae*, also known as Enzootic Pneumonia or EP.

2. Description of Related Art

It is known that the above-mentioned diseases can be prevented by immunization with vaccines. Vaccinating agents are usually provided for injection and have to be correspondingly sterile. Moreover, each individual injection causes stress to the creature being treated and for this reason the number of vaccination processes should be kept to a minimum.

One known possibility for reducing the number of vaccination processes are so-called combined vaccinations by which immunization against different diseases can be provided in just a few or even just one session. However, a combined vaccination is often not possible as a result of incompatibilities of different vaccines or components thereof with one another. Even if at least short-time compatibility can be achieved, these combination vaccines have to be produced on site. In the veterinary medical field, in particular, the vaccines then have to be prepared and/or administered outdoors. A problem here is that the combination vaccine may become contaminated, for example, with pathogens, particularly if a mixing vessel has to be punctured several times.

SUMMARY OF THE INVENTION

A primary object of the present invention is to provide a kit for preparing a vaccinating agent, a method of using this kit for preparing a vaccinating agent, a method of using two starting materials for preparing a vaccinating agent and a process for providing a vaccinating agent by which a vaccinating agent can be produced, even from starting materials which are only briefly stable with one another, by the simplest possible method, which is not prone to errors and is at the same time hygienic.

A first aspect the present invention relates to a kit for preparing a vaccinating agent, particularly for preparing a vaccinating agent for use in immunizing against the disease Porcine Circovirus Disease "PCVD" and/or Enzootic Pneumonia "EP" or against infections with Porcine Circovirus, particularly type 2, and/or *Mycoplasma hyopneumoniae*.

The kit according to the invention comprises a first starting material and a second starting material that is different from the first. A starting material for the purposes of the present invention is preferably any source material, particularly a vaccine, a source material comprising a vaccine and/or a component or source material for a vaccinating agent, preferably an antigen or a composition containing an antigen.

Moreover, the kit comprises a first container that is only partly filled with the first starting material and a second container comprising the second starting material.

A container for the purposes of the present invention is preferably a structure enclosing a volume, preferably configured to receive a liquid, particularly a vessel, a bottle, a bag or the like.

The kit further comprises an adapter device for establishing a fluid connection, wherein the fluid connection can be established between the first and second containers. It is also preferable that the adapter device should be configured to establish a fluid connection between the interiors of the first container and the second container.

Moreover, in the proposed kit, at least one of the containers is closed off by a factory-provided closure device. Preferably, both containers are closed off by a factory-provided closure device. Preferably, an airtight and/or sterile closure is provided. In particular this may be a seal, a rubber stopper or the like, wherein the closure device can preferably be penetrated and/or pierced through, particularly reversibly. In this way the containers, i.e., at least one of the containers can be sealed in sterile manner.

It is envisaged that the second container can be connected to the first container by means of the adapter device, when the closure device is pierced through for the first and/or only time, such that the second starting material enters the first container, particularly is transported therein, and there forms the vaccinating agent with the first starting material. The closure device or closure devices are thus preferably embodied to be penetrated or pierced by means of the adapter device. The adapter device is preferably configured to be able to penetrate and/or pierce the closure device or closure devices. In this way, a fluid connection can be provided between the first and second containers.

With the kit according to the invention, it is thus possible to prepare a vaccinating agent from two starting materials with only two containers and an adapter device, particularly for use in immunizing against the diseases caused by infections with Porcine Circovirus and/or *Mycoplasma hyopneumoniae*, preferably for use in immunizing against the diseases caused by infections with Porcine Circovirus and *Mycoplasma hyopneumoniae*. The kit also avoids the use of other incompatible starting materials, particularly by presenting the starting materials and containers in kit form.

Advantageously, the vaccinating agent may be formed in the only partly filled first container, avoiding the need for additional containers and/or additional adapter devices. This makes the application as simple as possible. In addition, the use of materials is minimized as the number of components required is reduced to a minimum.

Also, it is particularly advantageous that simply penetrating or piercing the closure device, for the first time or only once, is enough to produce the vaccinating agent. In fact, this avoids foreign substances or pathogens getting into the vaccinating agent during multiple penetration or piercing of the closure device.

In the present invention, for reasons of clarity, a distinction is made between vaccines as possible constituents of one or more starting materials and the vaccinating agent as the product prepared from the starting materials.

Thus, the term "vaccinating agent", even when it also denotes a vaccine, preferably denotes the end product that is preferably produced or prepared from the two starting materials and/or is used for the treatment. Particularly preferably, the vaccinating agent is a combination vaccine, preferably containing at least two vaccines different from one another or at least two antigens different from one another or two compositions containing antigen, where the compositions containing the antigen differ at least in the antigens present. The term "vaccines", even when it refers to vaccinating agents, preferably refers to starting materials or constituents thereof, particularly antigens or antigen-containing compositions. By an "antigen" or an "antigen-containing composition" is preferably meant a substance or a composition containing the substance which can elicit an immune response in an animal alter administration or can intensify an existing immune response. The differentiation between the terms "vaccinating agent" and "vaccine" thus, in particular, serves only to clarify or to distinguish the product from possible components of one or more of the starting materials. Consequently, it is possible to replace the term "vaccinating agent" by the term "vaccine" or vice versa.

A kit, under the terms of the present invention, is in particular a combination and/or system comprising the first container, the second container and preferably the adapter device, which form components of the kit. The components of the kit are preferably sold as a set, particularly in a combined package or the like. However, it is also possible for the components specified to form a loose combination for joint use. A common or linking component may be provided, for example, a common instruction manual, recommendations for use, references in the captions on one or more of the components of the kit or the like.

Another aspect of the present invention that can also be implemented independently relates to the use of a preferably proposed kit for the preparation and/or provision of a vaccinating agent, particularly for immunizing against the disease(s) Porcine Circovirus Disease "PCVD" and/or Enzootic Pneumonia "EP" or infections with Porcine Circovirus and/or infection with bacteria of the *Mycoplasma* strain, particularly *Mycoplasma* hyopneumoniae, preferably for immunization against the diseases Porcine Circovirus Disease "PCVD" and/or Enzootic Pneumonia "EP" or against infections with Porcine Circovirus, particularly Porcine Circovirus type 2 and infection with bacteria of the *Mycoplasma* strain, particularly *Mycoplasma hyopneumoniae*.

Another aspect of the present invention that can also be implemented independently relates to the use of at least two starting materials for preparing a vaccinating agent, particularly for simultaneous immunization, in particular, against the disease(s) Porcine Circovirus Disease "PCVD" and/or Enzootic Pneumonia "EP", preferably for in particular simultaneous immunization against the diseases Porcine Circovirus Disease "PCVD" and Enzootic Pneumonia "EP", or against infections with Porcine Circovirus, particularly Porcine Circovirus Type 2 and infection with bacteria of the *Mycoplasma* strain, particularly *Mycoplasma hyopneumoniae*, wherein the vaccinating agent is prepared using starting materials in containers and an adapter device. A kit may be used as proposed.

It is also envisaged that a first starting material is used in a first container only partly filled with the first starting material and a second starting material that is different from the first is used in a second container holding the second starting material- and an adapter device is used which is configured so as to establish a fluid connection between the first and second containers. At least one of the containers is closed off by a closure device. A fluid connection between the first and second containers is produced by means of the adapter device when the closure device is penetrated for the first and/or only time, in order to transfer the second starting material through the adapter device and closure device into the first container and produce the vaccinating agent in the first container.

Another aspect of the present invention that can also be implemented independently relates to a process for preparing a vaccinating agent from a first starting material and a second starting material different from the first, particularly for especially simultaneous immunization against the disease Porcine Circovirus Disease "PCVD" and/or Enzootic Pneumonia "EP", preferably for particularly simultaneous immunization against the diseases Porcine Circovirus Disease "PCVD" and Enzootic Pneumonia "EP". The vaccinating agent may be prepared using a kit as proposed.

A fluid connection is established between a first container only partly filled with the first starting material and a second container holding the second starting material by an adapter device when at least one closure device, which preferably closes off at least one of the containers and is provided on the operating side, is penetrated or pierced for the first and/or only time by the adapter device. The second starting material is transferred or conveyed through the adapter device and the closure device into the first container. In the first container, the vaccinating agent is formed from the first starting material and the second starting material.

Preferably, the first and/or second starting material is or comprises a vaccine, an antigen and/or an antigen-containing composition. Moreover, the first starting material may differ from the second starting material. The first starting material may thus be or comprise a first vaccine, a first antigen and/or a composition containing a first antigen and the second starting material may be or comprise a second vaccine, different from the first, a second antigen different from the first and/or an antigen-containing composition, the antigen of which differs from that of the first antigen-containing composition. Preferably, the first vaccine and the second vaccine, or the first antigen and the second antigen, or the compositions containing the various antigens are for particularly simultaneous immunization against various diseases or pathogens such as for example, against the disease Porcine Circovirus Disease "PCVD" and Enzootic Pneumonia "EP", or for immunization against Porcine Circovirus, preferably Porcine Circovirus type 2 and against Mycoplasmas, preferably against *Mycoplasma hyopneumoniae*. This makes it possible to produce a combination vaccine. The starting materials may contain other substances apart from vaccines, particularly water, adjuvants and/or excipients.

It is particularly preferable that the first starting material comprises only a first of the components *Mycoplasma* vaccine or *Mycoplasma* antigen, respectively, and Circovirus vaccine or Circovirus antigen, respectively, (and optionally other substances). The first starting material may thus comprise either *Mycoplasma* vaccine, or one or more *Mycoplasma* antigens or alternatively Circovirus vaccine or one or more Circovirus antigens. The first starting material is preferably stored separately from the second starting material, particularly if the starting materials are not stable together in the long term. The second starting material preferably only comprises the other of the components *Mycoplasma* vaccine or one or more *Mycoplasma* antigens, respectively, and Circovirus vaccine or one or more Circovirus antigens, respectively, (and optionally other substances). Thus, if the first starting material contains *Mycoplasma* vaccine or one or more *Mycoplasma* antigens, the second starting material contains Circovirus vaccine or one or more Circovirus antigens or vice versa.

The *Mycoplasma* vaccine may comprise attenuated and/or inactivated bacteria, fragments of bacteria or recombinantly produced parts of *Mycoplasma* hyopneumoniae, but at least one or more *Mycoplasma hyopneumoniae* antigens. Preferably, the *Mycoplasma hyopneumoniae* antigen originates from the *Mycoplasma hyopneumoniae* strain J or the inactivated *Mycoplasma hyopneumoniae* bacteria are those of the strain J. Moreover, the *Mycoplasma* vaccine may be one of the following vaccines or the *Mycoplasma* hyopneumoniae antigen may be the antigen or antigens contained in one of the following vaccines: Ingelvac® MycoFlex (Boehringer Ingelheim Vetmedica Inc, St Joseph, Mo., USA), Porcilis M. hyo, Myco Silencer® BPM, Myco Silencer® BPME, Myco Silencer® ME, Myco Silencer® M, Myco Silencer® Once, Myco Silencer® MEH (all from Intervet Inc., Millsboro, USA), Stellamune *Mycoplasma* (Pfizer Inc., New York, N.Y., USA), Suvaxyn *Mycoplasma*, Suvaxyn M. hyo, Suvaxyn MH-One (all previously from Fort Dodge Animal Health, Overland Park, Kans., USA (now Pfizer Animal Health).

The Circovirus vaccine may comprise attenuated and/or inactivated porcine Circovirus, preferably type 2, particularly type 2 ORF2 protein. It is particularly preferable to use recombinantly expressed ORF2 protein of Porcine Circovirus type 2, preferably expressed in and obtained from in vitro cell culture. Examples of ORF2 proteins of Porcine Circovirus type 2 are described inter alia in International Patent Application WO2006-072065. These have proved particularly advantageous for effective vaccination. Moreover, the Circovirus vaccine may be one of the following vaccines, or the Circovirus antigen may be the antigen or antigens contained in one of the following vaccines: Ingelvac®CircoFLEX, (Boehringer Ingelheim Vetmedica Inc, St Joseph, Mo., USA), CircoVac® (Merial SAS, Lyon, France), CircoVent (Intervet Inc., Millsboro, Del., USA), or Suvaxyn PCV-2 One Dose® (Fort Dodge Animal Health, Kansas City, Kans., USA).

The Circovirus vaccine, if it contains the ORF2 protein, preferably contains between 2 μg and 150 μg, preferably between 2 μg and 60 μg, more preferably between 2 μg and 50 μg, more preferably between 2 μg and 40 μg, more preferably between 2 μg and 30 μg, more preferably between 2 μg and 25 μg, more preferably between 2 μg and 20 μg, more preferably between 4 μg and 20 μg, more preferably between 4 μg and 16 μg ORF2 protein per dose to be administered. The Circovirus vaccine is preferably produced or designed so that 1 ml of the vaccine corresponds to a dose of 1 and/or one (single) dose. In particular the Circovirus vaccine may contain ORF2 protein in amounts of more than 2 μg/ml, preferably more than 4 μg/ml and/or less than 150 μg/ml, preferably less than 60 μg/ml, 50 μg/ml, 40 μg/ml, 30 μg/ml or 25 μg/ml, particularly less than 20 μg/ml. This helps to ensure reliable administration.

The *Mycoplasma* vaccine, if it contains inactivated *Mycoplasma* bacteria, preferably inactivated *Mycoplasma hyopneumoniae* bacteria, preferably contains between $10^3$ and $10^9$ colony forming units (CFU), preferably between $10^4$ and $10^8$ (CFU), more preferably between $10^5$ and $10^6$ (CFU) per dose to be administered, the corresponding CFU being selected before the inactivation of the bacteria. The *Mycoplasma* vaccine is preferably prepared or designed such that 1 ml of the vaccine corresponds to a dose of 1 and/or one (single) dose. In particular, the mycoplasma vaccine may contain more than $10^3$ CFU/ml, preferably more than $10^4$ CFU/ml, particularly more than $10^5$ CFU/ml and/or less than $10^9$ CFU/ml, preferably less than $10^8$ CFU/ml, particularly less than $10^7$ CFU/ml or $10^6$ CFU/ml inactivated *Mycoplasma* bacteria, preferably inactivated *Mycoplasma hyoneumoniae* bacteria, particularly before the inactivation of the bacteria.

At least one of the starting materials and/or the vaccinating agent may contain an adjuvant, preferably a polymeric adjuvant, particularly carbomer. Preferably, at least or exactly one of the two starting materials, preferably both starting materials, contain a quantity of adjuvant of 500 μg to 5 mg, preferably 750 μg to 2.5 mg, more preferably about 1 mg of adjuvant per dose to be administered. The starting materials are preferably prepared or designed such that 1 ml of the respective starting material corresponds to a dose of 1 and/or one (single) dose. The use of an adjuvant, preferably a polymeric adjuvant, such as carbomer, for example, has proved advantageous in terms of the efficiency of the immunization or its duration of effect. The use of alternative and/or additional adjuvants is not excluded, however.

It has also proved advantageous if the total volume of the first container exceeds the volume of the first starting material at least by the volume of the second starting material, particularly by more than 2%, preferably more than 5%, particularly more than 8%. This ensures that the first container has sufficient capacity for the second starting material. In addition, the volume of the first container, which exceeds the sum of the volumes of the first and second starting material, ensures effective mixing of the starting material, particularly when the first container is moved after the transfer of the second starting material into the first container.

Thus, it is preferable, on the one hand, that the total volume of the first container should exceed the sum of the volumes of the starting materials. On the other hand, the first container is moved during and/or after the transfer of the second starting material into the first container, to achieve or speed up homogeneous mixing and/or reaction.

According to another aspect of the present invention, the first container may be used for installation in or use with an injection device. In particular, this is an injection device for multiple use, such as, for example, an injection gun, a pressure injection and/or a self-filling syringe as used for example, for vaccinating larger herds of animals. In this way, the number of penetrations of the closure device of the first container can be minimized. In particular, the number of penetrations can be reduced to two, namely one penetration for the preparation process and a second penetration for drawing up the vaccinating agent. Particularly, advantageously, the adapter device may be used for connection to the injection device, thus reducing the number of penetrations to one.

The kit according to the invention may comprise an injection device or be associated with one such. In particular, an opening, a flange or other connecting or closure element of the first container and/or the adapter device may be configured so as to allow direct use in or with an injection device. Moreover, the opening, the flange or the other connecting and/or closure element may be specifically designed for connection to a particular injection device. Once again this decreases the likelihood of incorrect use, particularly of incorrect amounts of active substance or methods of administration.

One or more of the containers may contain, in addition to the respective starting material, a gas, particularly a protective gas, thus making it possible to improve the long-term stability of the respective starting material. Moreover, the adapter device may be embodied to transfer the gas from the first container into the second container when the second starting material is transferred from the second container into the first container, particularly with the exclusion of the surrounding atmosphere. Thus ensures that effects on one or more of the starting materials and/or the vaccinating agent as a result of oxidation or the like, in particular, is ruled out and/or a pressure equalization is made possible.

Further aspects, details, features, properties and advantages of the present invention will become apparent from the following description of a preferred embodiment of the proposed kit for preparing a vaccinating agent in conjunction with the accompanying drawings.

DETAILED DESCRIPTION OF THE INVENTION

Figure 1:
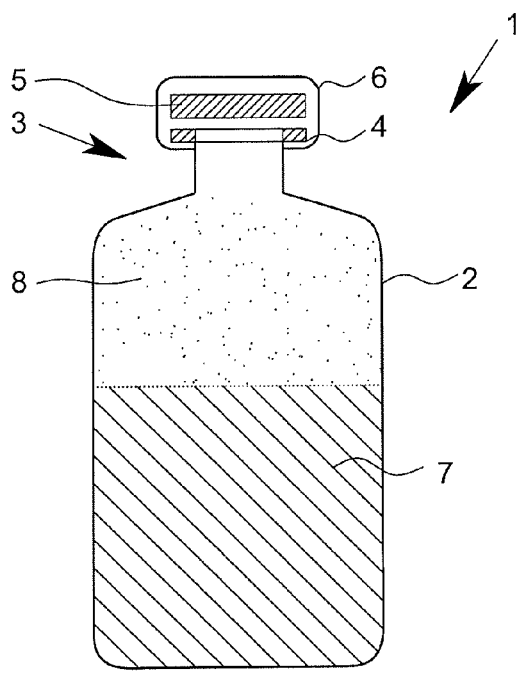
FIG. 1 is a schematic representation of a first container, partly filled with a first starting material.

In the Figures, the same reference numerals are used for identical or similar parts, where corresponding or comparable properties and advantages are obtained even if the description is not repeated.

FIG. 1 shows a first container 1 with a wall 2 delimiting a volume. The container 1 comprises an opening region 3 which may have a flange 4, for example, an annular shoulder. Preferably, the container 1 is closed off by a closure device 5, particularly in sterile and/or airtight manner. For this purpose, it may be envisaged that the closure device 5 abuts firmly on the flange 4, more particularly is pressed against it.

For example, a clamping element 6, particularly a clamping ring, may be provided which presses the closure device 5 against the flange 4. The clamping element 6 may be metallic and may contain aluminum or stainless steel, in particular. Alternatively or additionally, it is possible for the clamping element 6 to include plastics or be made of plastics. The clamping element 6 is preferably embodied so as to pressure the closure device 5 against the flange 4 and thereby enable the first container 1 to be sealed off, particularly from the environment and/or atmosphere.

In the embodiment shown, the closure device 5 closes off or seals the first container 1. The closure device 5 is preferably penetrable or pierceable, for example, with a spike, a needle, a hollow needle, a double spike or the like. Particularly preferably, the closure device 5 is configured to be penetrable or pierceable in such a way as to achieve a reversible closure, i.e., even after penetration or piercing and removal of the corresponding agent, the closure device 5 particularly makes it possible to obtain an, in particular, airtight and/or sterile seal. The closure device 5 may contain rubber, particularly halobutyl type 1 rubber and/or may be in the form of a rubber stopper. However, the closure device 5 may also be made of or contain other materials, particularly materials that are also used for the wall 2.

Figure 7:
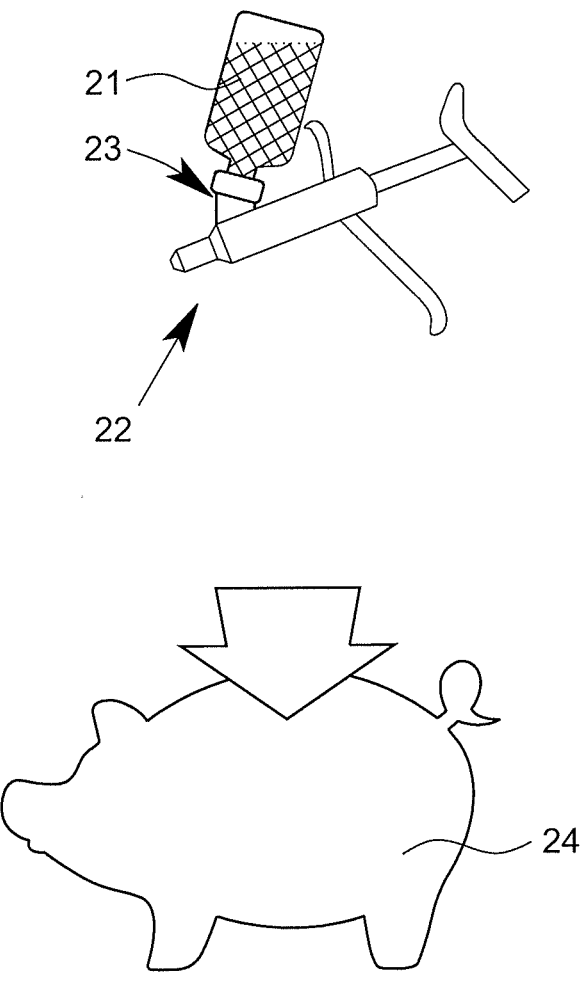
FIG. 7 is a schematic representation of an injection device with the first container attached.

The wall 2 of the first container 1 preferably comprises a sterilizable material, preferably glass, polyethylene, high density polyethylene (HDPE), ethylenevinylacetate (EVA), halobutyl type 1 rubber and/or siliconized chlorobutyl. The wall 2 may be of rigid or flexible construction. The first container 1 may be embodied, in particular, as a bottle, bag, can or the like. In particular, the first container 1 may be a cartridge, an insert or an installation or attachment device for an injection device 22 (cf. FIG. 7), as will be discussed in more detail hereinafter.

In the embodiment shown in FIG. 1, the container 1 is only partly filled with a first starting material 7. The container 1 is, for example, filled with the first starting material to an amount of less than 70%, preferably less than 50%, particularly less than 45% and/or more than 10%, preferably more than 20%, particularly more than 30%.

Besides the first starting material, the first container 1 may contain a gas 8, particularly a protective gas, noble gas, inert gas or the like. In this way, the shelf life of the first starting material 7 can be improved.

Preferably, the sum of the volumes of the first starting material 7 and the gas 8 gives the total volume of the first container 1, preferably therefore the volume enclosed by the wall 2 of the first container 1, particularly with the closure device 5, or a smaller volume.

Figure 2:
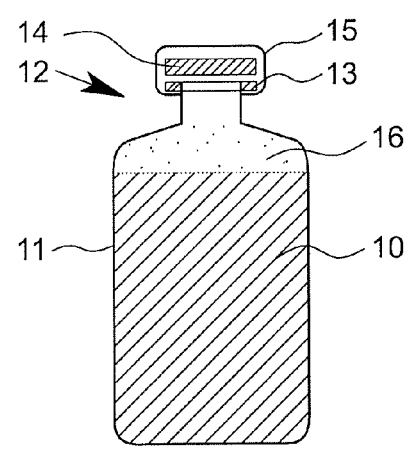
FIG. 2 is a schematic representation of a second container with a second starting material.

FIG. 2 shows a second container 9 with a second starting material 10. The second container 9 may comprise a wall 11, an opening region 12, a flange 13, a closure device 14 and/or a clamping element 15, which may preferably have the same or similar properties to the corresponding elements of the first container 1, and for this reason the description will not be repeated at this point. Therefore, only possible differences between the second container 9 and the first container 1 will be mentioned hereinafter.

The second container 11 is preferably configured with an at least partially flexible wall 11 wherein, in particular, pressure can be exerted on the second starting material 10 by pressing on the wall 11. This can help to promote the expulsion or transfer of the second starting material 10.

Preferably, the volume of the gas 8 corresponds to or exceeds the volume of the second starting material 10. In particular, the volume of the gas 8 in the first container 1 exceeds the volume of the second starting material 10 by more than 2%, preferably more than 5%, particularly more than 8% and/or less than 80%, preferably less than 50%, particularly less than 40% or 30%. This allows the first container 1 to take up minimal space while at the same time preparing the vaccinating agent 21 (cf. FIG. 5) in the first container 1. In particular, a sufficient volume of gas 8 remains in the first container 1, thus allowing homogeneous mixing by movement of the first container 1.

In the embodiment shown in FIG. 2, the second container 9 is at least substantially filled with the second starting material 10. Alternatively or additionally, however, it is also possible for the second container 9 to be completely filled with the second starting material 10 or only partly filled with the second starting material 10. If the second container 9 is only partly filled with the second starting material 10, a gas 16, particularly a protective gas, may be provided which preferably fills the volume of the second container 9 enclosed by the wall 11, particularly with the closure device 14, together with the second starting material 10.

It is particularly preferred if the total volume of the first container 1 exceeds the volume of the first starting material 7 at least by the volume of the second starting material 10.

The volume of the first container 1 thus preferably exceeds the total of the volumes of the first starting material 7 and second starting material 10.

Figure 3:
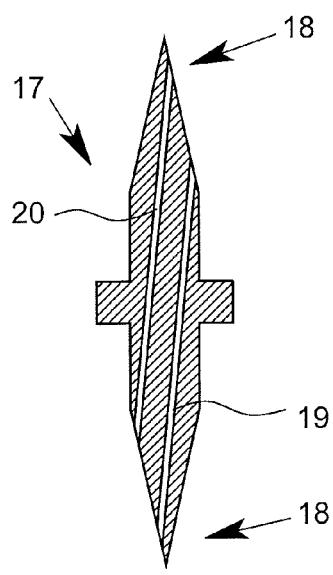
FIG. 3 is a cross-sectional view of an adapter device for fluidically connecting the first and second containers.

FIG. 3 shows an adapter device 17 for providing a fluidic connection between the first container 1 and the second container 9. The adapter device 17 may comprise at least one, preferably two, but also more than two adapter elements 18, particularly needles, hollow needles, spikes, wedges or the like, conical spikes being represented in FIG. 3.

The adapter device 17 preferably comprises a fluid channel 19, particularly for fluidically connecting the interiors of the containers 1, 9. The adapter device 17 is in the form of a double spike or hollow needle in the embodiment shown.

The adapter device 17 may be configured so that, during the transfer of the second starting material 10 into the first container 1, the gas 8 or protective gas passes, or more particularly is transported, from the first container 1 into the second container 9. For this purpose the adapter device 17 may comprise a venting and/or exhaust device 20. The venting and/or exhaust device 20 is preferably in the form of a channel, particularly at least substantially parallel to the fluid channel 19. However, other solutions are also possible.

Preferably, the adapter device 17 comprises a channel as the venting and/or exhaust device 20, the openings of which are arranged so that when the second starting material 10 flows out of the second container 9 under the influence of gravity this allows a backflow of the gas 8 from the first container 1 into the second container 9. In particular, the opening of the venting and/or exhaust device 20 facing the first container 1 may be recessed relative to the opening of the fluid channel 19 facing the first container 1 in the direction of the longitudinal extent of the adapter device 17 or may be arranged on the side of the opening of the fluid channel 19 remote from the open end of the adapter device 17. The opening of the venting and/or exhaust device 20 facing the second container 9, by contrast, is preferably arranged closer to the open end of the adapter device 17 in relation to the opening of the fluid channel 19 facing the second container 9.

The adapter device 17 in the embodiment shown in FIG. 3 is formed in one piece. However, it is also possible, alternatively or additionally, for a hose, a tube, or some other flexible or rigid transition to be provided between the adapter elements 18. Preferably, the fluid channel 19 and/or the venting and/or exhaust device 20 connect(s) the adapter elements 18 with no interruptions. In particular, it is possible for a hose, tube or the like to be provided, particularly molded on, between the adapter elements 18. This permits flexible handling and/or extension of the adapter device 17.

The adapter device 17, particularly one or more of the adapter elements 18, may be configured specifically for the first container 1 and/or for the second container 9. This can be achieved in particular by mechanically configuring at least one of the adapter elements 18 specifically for one of the containers 1, 9, particularly for one of the containers 1, 9 which is associated with the respective adapter element 18, for example, by means of a specific thread 3, 12, a specific projection, undercut, a specific lug or other structure. In this way, substances other than the first starting material 7 and/or the second starting material 10 can be prevented from getting into the first container 1 and/or the second container 9. It is also preferable that the opening region of at least one or both containers 1, 9 is specifically configured for the adapter device 17, particularly for an adapter element 18.

It is also preferable for a connection to be provided only between the containers 1, 9, preferably with exclusion of the surrounding atmosphere. For the purposes of the present invention, the atmosphere is preferably already deemed to be excluded even when there is still a slight residual volume of atmospheric origin remaining in the adapter device 17, for example, less than 10 ml or 5 ml.

The first starting material 7 and/or the second starting material 10 preferably comprise a vaccine. It is also preferable that the starting materials 7, 10 should be different, and in particular, should contain different vaccines.

Figure 4:
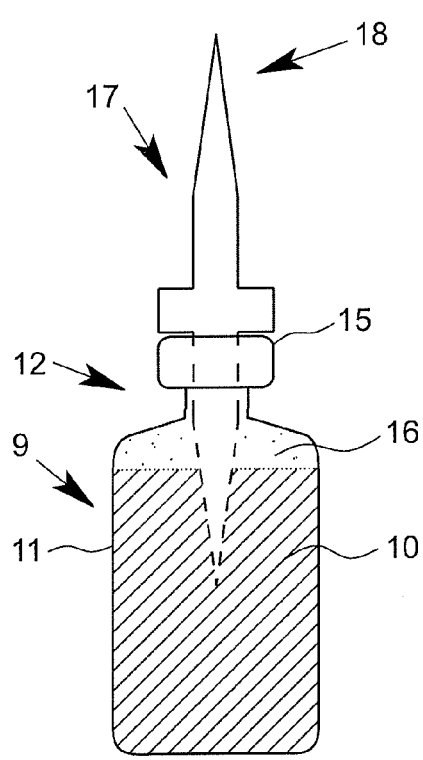
FIG. 4 shows the second container with adapter device inserted.
Figure 5:
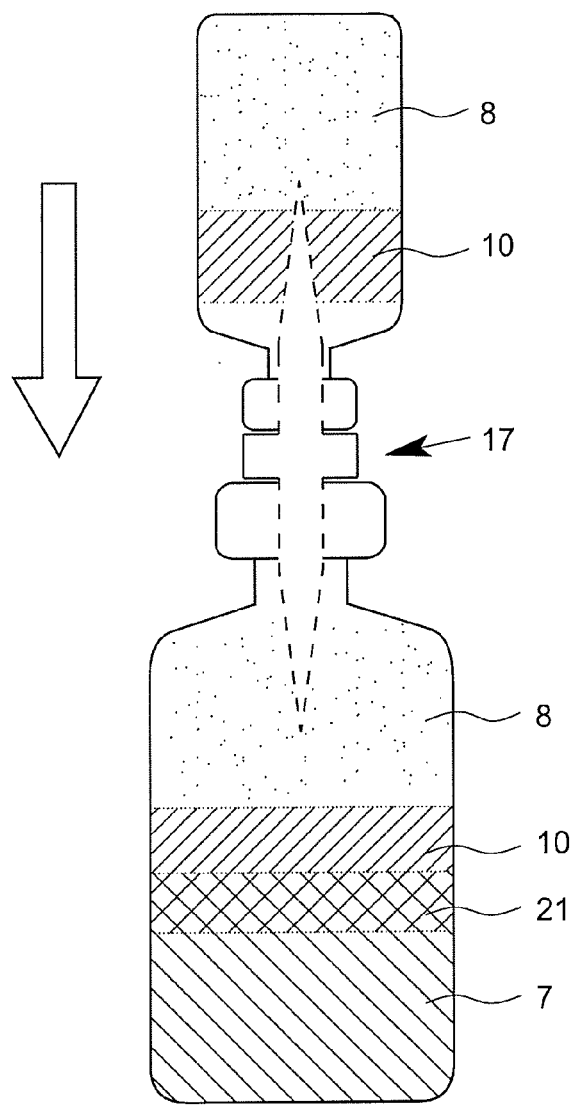
FIG. 5 shows the first and a second container connected by the adapter device.

As shown in FIGS. 4 & 5, the adapter device 17 can be used to provide a fluid connection between the first container 1 and the second container 9, wherein the second starting material 10 can preferably be transported into the first container 1 with the assistance of gravity and/or by the exerting of pressure on the second starting material 10 through the wall 11 of the second container 9, in order to form the vaccinating agent 21 with the first starting material 7. The vaccinating agent 21 is preferably intended for preventing pigs becoming ill with infections of *Mycoplasma hyopneumoniae* and/or Porcine Circovirus, particularly type 2, preferably to prevent pigs becoming ill with infections of *Mycoplasma* hyopneumoniae and Porcine Circovirus type 2, i.e., in the embodiment shown it is a combination vaccine.

The first container 1, the second container 9, and preferably, the adapter device 17 preferably form a kit or set, and thus, preferably, have at least one linking common feature for the purposes of the present invention. This common feature may be that the first container 1, the second container 9 and/or the adapter device 17 are packaged together. Alternatively or additionally, it is possible that the first container 1, the second container 9 and/or the adapter device 17 have the same operating instructions, the same in-pack leaflet, the same manufacturer's recommendations or the like. It is also possible for captions, label markings, symbols or other information on the containers 1, 9 to cross-reference one another or the like.

Optionally, the kit may also comprise other components. Examples of these are one or more injection devices 22, adapter devices for connecting the first container 1 to an injection device 22, some other device or another container.

The kit is preferably intended for preparing a vaccinating agent 21 for preventing diseases caused by infections with Porcine Circovirus type 2 and/or *Mycoplasma* hyopneumoniae, preferably for preventing diseases caused by infections with Porcine Circovirus type 2 and/or *Mycoplasma hyopneumoniae* in pigs. However, different applications are not excluded. In particular, it may alternatively be envisaged to use substances other than the vaccines specified or substances or substance mixtures other than starting materials 7, 10, and/or to obtain advantages in respect of ease of handling and the reduced likelihood of an ingress of foreign substances, pathogens or the like. In particular, the alternative starting materials may be one or more antigens of the following pathogens: *Actinobacillus pleuropneumonia* (A1); Adenovirus (A2); Alphavirus such as, for example, Eastern Equine Encephalomyelitis Virus (A3); *Bordetella bronchiseptica* (A4); *Brachyspira* spp. (A5), preferably *B. hyodysentheriae* (A6); *B. piosicoli* (A7), *Brucella suis*, preferably the biovars 1, 2, and 3 (A8); Classical Swine Fever Virus (A9); *Clostridium* spp. (A10), preferably *Cl. difficile* (A11), *Cl. perfringens* of types A, B, and C (A12), *Cl. novyi* (A13), *Cl. septicum* (A14), *Cl. tetani* (A15); Coronavirus (A16), preferably Porcine Respiratory Corona Virus (A17); *Eperythrozoonosis suis* (A18); *Erysipelothrix rhusiopathiae* (A19) *Escherichia coli* (A20); *Haemophilus parasuis*, preferably of subtypes 1, 7 and 14 (A21) Hemagglutinating Encephalomyelitis Virus (A22); Japanese Encephalitis Virus (A23); *Lawsonia intracellularis* (A24); *Leptospira* spp. (A25), preferably *Leptospira australis* (A26), *Leptospira canicola* (A27), *Leptospira grippotyphosa* (A28), *Leptospira icterohaemorrhagicae* (A29), *Leptospira interrogans* (A30), *Leptospira pomona* (A31), *Leptospira hardjo* (A32) and *Leptospira tarassovi* (A33); *Mycobacterium* spp. (A34) preferably *M. avium* (A35) and *M. intracellulare* (A36); *Pasteurella multocida* (A37); Porcine Cytomegalovirus (A38); Porcine Parvovirus (A39); Porcine Reproductive and Respiratory Syndrome (PRRS) Virus (A40); Pseudorabies Virus (A41); Rotavirus (A42); *Salmonella* spp. (A43), preferably *S. thyphimurium* (A44) and *S. choleraesuis* (A45); *Staphylococcus* spp. (A46) preferably *Staph. hicus* (A47); *Streptococcus* spp. (A48), preferably *Strep. suis* (A49); Swine Herpes Virus (A50); Swine Influenza Virus (A51); Swine Pox Virus (A52); Vesicular Stomatitis Virus (A53); Vesicular exanthema of swine virus (A54); and *Mycoplasma* hyosynoviae (A55). Preferably, the starting materials 7, 10, are different antigens of the pathogens listed here, so that after the mixing of the different starting materials the vaccinating agent 21 can be used for preventing diseases caused by at least two of the pathogens listed here.

To prepare the vaccinating agent 21, the adapter device 17 with an adapter element 18 may be pushed through the closure device 14 of the second container 9 into the interior thereof, particularly as shown in FIG. 4. The closure device 14 is thus preferably penetrated by the adapter device 17, particularly an adapter element 18 thereof.

Moreover, in particular, as shown in FIG. 5, the combination of the second container 9 and adapter device 17, particularly with another adapter element 18 of the adapter device 17, may be pushed through the closure device 5 of the first container 1 into the interior thereof. Preferably, the adapter device 17 or the adapter element 18 penetrates the closure device 5 of the first container 1. In this way it is possible for the adapter device 17 to provide a fluid connection 20 between the interiors of the first container 1 and the second container 9.

In FIGS. 4 & 5, details of the opening regions 3, 12 of the containers 1, 9 and the adapter device 17 are not shown, for reasons of clarity. Reference is made to FIGS. 1 to 3 on this subject.

As shown in FIG. 5, the second starting material 10 may be transferred through the adapter device 17 into the first container 1, preferably using gravity and/or by compression of the preferably flexibly formed second container 9. Alternative and/or additional methods or procedures for transferring the second starting material 10 into the first container 1 are also possible.

In another example, first the adapter device 17 is used to penetrate the closure device 5 of the first container 1. In a second step the second container 9 is then fitted onto the adapter device 17 already inserted into the first container 1 or is otherwise connected to the adapter device 17 such that a fluidic connection 20 is formed between the first container 1 and the second container 9. In each case, it is preferable, after inserting the adapter device 17 into a first of the containers 1, 9, that the one of the containers 1, 9 that is not yet attached to the adapter device 17 is fitted onto the vertically positioned combination of adapter device 17 and the other one of the containers 1, 9. This prevents one of the starting materials 7, 10 from flowing out.

In one aspect, the present invention relates to the penetration, for the first and/or only time, of at least one of the closure devices 5, 14 by the adapter device 17. Particularly preferably, both containers 1, 9 comprise closure devices 5, 14, which are each penetrated, pierced or perforated for the first and/or only time. This is made possible, in the embodiment shown, by the fact that the first container 1 is only partly filled with the first starting material 7. Advantageously, this makes it possible to produce the vaccinating agent 21, particularly the combination vaccine, without having to use a plurality of adapter devices 17 or more than two containers 1, 9. This results in a simple, reliable and clear operation, in which the vaccinating agent 21 is prepared using only one adapter device 17, thus effectively preventing mix-ups with other starting materials and the introduction of impurities or pathogens.

These positive properties can be further enhanced if the first container 1, optionally with the adapter device 17, is configured to be used directly in the injection device 22, particularly in an injection gun, in a pressure injector and/or in a self-filling syringe (cf. FIG. 7) or with these devices. The first container 1 can thus be used in or with a preferably multiple-use injection device 22. This means that each closure device 5, 14 only has to be pierced or penetrated on only a first occasion. This allows a high degree of safety of use, ease of handling and hygiene.

It may be envisaged that the first container 1 is configured for use in or with an injection device 22 in a neck or mouth region, particularly in the opening region 3, for connection to an in particular multiple-use injection device 22. The injection device 22 may have a receptacle 23 for the first container 1. It may be provided that the longitudinal extent and/or the diameter of the first container 1 is configured for use in an injection device 22 that is, in particular, designed for multiple use. For example, the first container 1 may have a diameter of more than 1 cm, preferably more than 2 cm, particularly more than 3 cm and/or less than 10 cm, preferably less than 8 cm, particularly less than 6 cm. Alternatively or additionally, it is possible for the first container 1 to have a longitudinal extent which is more than 3 cm, preferably more than 5 cm, particularly more than 6 cm and/or less than 30 cm, preferably less than 25 cm, particularly less than 20 cm.

Figure 6:
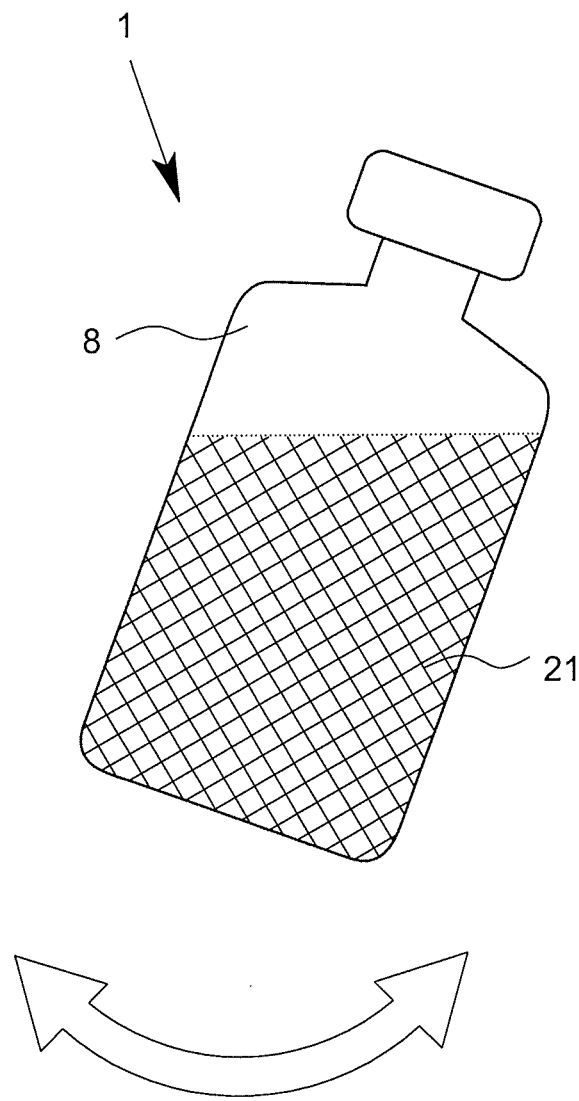
FIG. 6 the first container with a vaccinating agent.

As soon as the second starting material 10 has passed through the adapter device 17 into the first container 1, vaccinating agent 21 can be formed. It is possible that the vaccinating agent 21 is produced by mixing the starting materials 7, 10, by dissolving the starting materials 7, 10 in one another and/or by reacting the starting materials 7, 10 or parts thereof with one another. Preferably, as shown by the arrow in FIG. 6, the first container 1 holding the starting materials 7, 10 is set in motion, particularly shaken, tilted, set in rotation or the like. This ensures or assists with homogeneous and/or faster mixing, reaction and/or dissolving.

In the embodiment shown, the first starting material 7 and/or the second starting material 10 comprises vaccine preferably in amounts of more than 30 per cent by weight, preferably more than 40 per cent by weight, particularly more than 50 per cent by weight; and/or less than 90 per cent by weight, preferably less than 80 per cent by weight, particularly less than 70 per cent by weight. Moreover, the first starting material 7, the second starting material 10, and/or the vaccinating agent 21 formed thereby may be a suspension, preferably with vaccines and/or insoluble proteins, preferably in amounts of more than 30 per cent by weight, preferably more than 40 per cent by weight, particularly more than 50 percent by weight; and/or less than 90 per cent by weight, preferably less than 80 per cent by weight, particularly less than 70 per cent by weight. This ensures an efficacy, with small amounts of vaccinating agent, and at the same time, low enough viscosity, which assists with administration.

The second starting material 10 preferably comprises only the other one of the components Mycoplasma vaccine or Mycoplasma antigen and Circovirus vaccine or Circovirus antigen. It is also preferable if the first starting material 7 comprises Mycoplasma vaccine or one or more Mycoplasma antigens, the first starting material 7 does not comprise Circovirus vaccine or Circovirus antigen, but for this purpose the second starting material 10 comprises Circovirus vaccine or one or more Circovirus antigens, but not Mycoplasma vaccine or Mycoplasma antigen. However, it is not ruled out, for any of the starting materials 7, 10, that the particular starting material should not contain additional substances. These might be water, excipients, adjuvants, preservatives or the like.

In one embodiment, the ratio by volume of the first starting material 7 to the second starting material 10 is 3:1 to 1:3, preferably 2:1 to 1:2, particularly about 1:1. The first starting material 7 and/or the second starting material 10 and/or the vaccinating agent 21 may have a viscosity that is less than 10,000 mPa·s, preferably less than 1000 mPa·s, particularly less than 500 mPa·s; and/or more than 5 mPa·s, preferably more than 10 mPa·s, particularly more than 20 mPa·s, measured with a Brookfield viscometer according to EN ISO 2555 at 5° C. Preferably, the first starting material 7 and/or the second starting material 10 are liquid at 2° C. to 8° C. and/or have a melting point which is less than 1° C., preferably less than 0° C., particularly less than −0.2° C. and/or higher than −1.5° C., preferably higher than −1° C., particularly higher than −0.8° C.

According to another aspect of the present invention, it is preferable that the vaccinating agent 21 has a characteristic color which is different from the two starting materials 7, 10. The specific color of the vaccinating agent may be formed, for example, by mixing the differently colored starting materials 7, 10. For example, mixing a yellow starting material 7 with a red starting material 10 results in a vaccinating agent 21 that is orange in color. It is possible for dye components in the starting materials 7, 10 to produce the characteristic color by reaction or other interactions during the preparation of the vaccinating agent 21. Alternatively or additionally, the vaccinating agent 21, in contrast to at least one of the starting materials 7, 10, may have one color or no color. As a result, by means of the characteristic color, it is possible to ensure that the vaccinating agent 21 has been successfully prepared. This is also possible if at least one of the starting materials has a color but, once prepared, the vaccinating agent 21 does not.

As already stated above, the Mycoplasma vaccine may comprise attenuated and/or inactivated bacteria, fragments of bacteria or recombinantly prepared parts of Mycoplasma hyopneumoniae, but at least one or more Mycoplasma hyopneumoniae antigens. Preferably, the Mycoplasma hyopneumoniae antigen originates from the Mycoplasma hyopneumoniae strain J, or the inactivated Mycoplasma hyopneumoniae bacteria are those of the strain J. Moreover, the Mycoplasma vaccine may be one of the following vaccines or the Mycoplasma hyopneumoniae antigen may be the antigens contained in one of the following vaccines: Ingelvac® MycoFlex (Boehringer Ingelheim Vetmedica Inc, St Joseph, Mo., USA), Porcilis M. hyo, Myco Silencer® BPM, Myco Silencer® BPME, Myco Silencer® ME, Myco Silencer® M, Myco Silencer® Once, Myco Silencer® MEH (all obtainable from Intervet Inc., Millsboro, USA) Stellamune Mycoplasma (Pfizer Inc., New York, N.Y., USA), Suvaxyn Mycoplasma, Suvaxyn M. hyo, Suvaxyn MH-One (all formerly from Fort Dodge Animal Health, Overland Park, Kans., USA (now Pfizer Animal Health).

The Circovirus vaccine may comprise attenuated and/or inactivated porcine Circovirus, preferably type 2, particularly type 2 ORF2 protein. It is particularly preferable to use recombinantly expressed ORF2 protein of Porcine Circovirus type 2, preferably expressed in and/or obtained from in vitro cell culture. Examples of ORF2 proteins of Porcine Circovirus type 2 are described inter alia in International Patent Application WO2006-072065. These have proved particularly advantageous for effective vaccination. Moreover, the Circovirus vaccine may be one of the following vaccines, or the Circovirus antigen may be the antigen or antigens present in one of the following vaccines: Ingelvac®CircoFLEX, (Boehringer Ingelheim Vetmedica Inc, St Joseph, Mo., USA), CircoVac® (Merial SAS, Lyon, France), CircoVent (Intervet Inc., Millsboro, Del., USA), or Suvaxyn PCV-2 One Dose® (Fort Dodge Animal Health, Kansas City, Kans., USA).

The Circovirus vaccine, if it contains the ORF2 protein, preferably contains between 2 µg and 150 µg, preferably between 2 µg and 60 µg, more preferably between 2 µg and 50 µg, more preferably between 2 µg and 40 µg, more preferably between 2 µg and 30 µg, more preferably between 2 µg and 25 µg, more preferably between 2 µg and 20 µg, more preferably between 4 µg and 20 µg, more preferably between 4 µg and 16 µg of ORF2 protein per dose to be administered. The Circovirus vaccine is preferably prepared or designed so that 1 ml of the vaccine corresponds to a dose of 1 and/or one (single) dose.

The Mycoplasma vaccine, if it contains inactivated Mycoplasma bacteria, preferably inactivated Mycoplasma hyopneumoniae bacteria, preferably contains between $10^3$ and $10^9$ colony forming units (CFU), preferably between $10^4$ and $10^8$ (CFU), more preferably between $10^5$ and $10^6$ (CFU) per dose to be administered, the corresponding CFU being adjusted before the inactivation of the bacteria. The Mycoplasma vaccine is preferably prepared or designed so that 1 ml of the vaccine corresponds to a dose of 1 and/or one (single) dose.

The Mycoplasma vaccine may preferably comprise attenuated and/or inactivated bacteria or fragments of bacteria of the strain Mycoplasma hyopneumoniae or corresponding antigens, preferably in amounts of more than 30 per cent by weight, preferably more than 40 per cent by weight, particularly more than 50 per cent by weight; and/or less than 90 per cent by weight, preferably less than 80 per cent by weight, particularly less than 70 per cent by weight.

The Circovirus vaccine may preferably comprise attenuated and/or inactivated Porcine Circovirus, preferably type 2, particularly Porcine Circovirus type 2 ORF2 protein or corresponding antigens, preferably in amounts of more than 30 per cent by weight, preferably more than 40 per cent by weight, particularly more than 50 per cent by weight; and/or less than 90 per cent by weight, preferably less than 80 per cent by weight, particularly less than 70 per cent by weight.

Moreover, at least one of the starting materials 7, 10 and/or the vaccinating agent 21 may comprise one, preferably polymeric, adjuvant, particularly carbomer. Preferably one of the two starting materials or, more preferably both starting materials, contain an amount of adjuvant of from 500 µg to 5 mg, preferably from 750 µg to 2.5 mg, more preferably about 1 mg per dose to be administered. The starting materials are preferably prepared or designed so that 1 ml of the respective starting material corresponds to a dose of 1 and/or one (single) dose. In particular, at least one of the starting materials 7, 10 may thus comprise one or more adjuvants in a total amount of more than 500 µg/ml, preferably more than 750 µg/ml and/or less than 5 mg/ml, preferably less than 2.5 mg/ml.

It is also possible for at least one of the starting materials 7, 10 and/or the vaccinating agent 21 to contain an adjuvant in amounts of more than 0.1 per cent by weight, preferably more than 1 per cent by weight, particularly more than 2 per cent by weight; and/or less than 20 per cent by weight, preferably less than 10 percent by weight, particularly less than 5 per cent by weight. It is also possible for a preferably polymeric adjuvant, particularly carbomer, to be formed in the vaccinating agent 21.

The *Mycoplasma* vaccine and/or the Circovirus vaccine or at least one of the starting materials 7, 10, and/or the vaccinating agent 21 may contain formaldehyde, preferably in a concentration of less than 2.5 mg/m$^3$, preferably less than 1.5 mg/m$^3$, particularly 0.74 mg/m$^3$ or less. Alternatively or additionally, at least one of the starting materials 7, 10, preferably both starting materials 7, 10, may contain water in a concentration of at least 20 per cent by weight, preferably at least 30 per cent by weight, particularly at least 40 per cent by weight; and/or at most 80 per cent by weight, preferably at most 70 per cent by weight, particularly at most 60 per cent by weight.

The first starting material 7, the second starting material 10 and/or the vaccinating agent 21 may comprise one or more excipients, particularly a preservative, an antioxidant and/or an emulsifier, preferably in a concentration of at least 0.1 per cent by weight, preferably at least 0.2 per cent by weight, particularly at least 0.3 per cent by weight; and/or at most 10 per cent by weight, preferably at most 5 per cent by weight, particularly at most 3 per cent by weight.

The preferred use of the present invention is in the preparation of the vaccinating agent 21 from two vaccines, particularly preferably the preparation of a vaccinating agent 21 for use in the in particular simultaneous immunization against Porcine Circovirus Disease "PCVD" and/or Enzootic Pneumonia "EP" or against infection with Porcine Circovirus and/or with *Mycoplasma* bacteria, preferably for use in immunization against the disease Porcine Circovirus Disease "PCVD" and Enzootic Pneumonia "EP" or against infection with Porcine Circovirus, particularly type 2, and with *Mycoplasma* bacteria, particularly *Mycoplasma hyopneumoniae*. Moreover, the present invention relates primarily to vaccinating agents for veterinary medicine, particularly for use in pigs.

However, the present invention is not restricted to this combination. In particular, it is possible to use the proposed kit with other starting materials, particularly vaccines or antigens, such as for example, with antigens of the pathogens described above. Here, too, it may be possible to achieve similar advantages at least in respect of ease of use and especially hygienic use. The same also applies to the aspect of the present invention that the vaccinating agent 21 prepared has a different color from the starting materials 7, 10, thus providing an efficient, simple and effective method of checking that the vaccinating agent 21 has been successfully prepared. The specific color of the vaccinating agent may result for example, from mixing the differently colored starting materials 7 and 10. For example, by mixing a yellow starting material 7 with a red starting material 10, a vaccinating agent 21 having an orange color is produced. The use of the first container 1 with an injection device 22 may also be applied successfully and advantageously to other fields, wherein similar advantages may be achieved particularly in respect of improved hygiene and/or reduced use of materials. However, it is particularly preferable to combine the proposed kit with a characteristic color for the vaccinating agent 21 prepared which is different from the colors of the starting materials 7, 10. This results in an exceptionally high degree of certainty in use. However, the individual aspects of the present invention may also be combined in any other desired manner.

Further aspects of the present invention include a kit for preparing a vaccinating agent, the kit comprising a first starting material, a second starting material different from the first, a first container only partly filled with the first starting material, a second container comprising the second starting material and preferably an adapter device for providing a fluid connection between the first and second container, wherein at least one of the containers is closed off with a factory-provided closure device and the second container is connectable to the first container by means of the adapter device by piercing the closure device for the first and/or only time, such that the second starting material enters the first container and there forms the vaccinating agent with the first starting material, preferably wherein the first and/or second starting material is or comprises a vaccine; and/or wherein the first starting material differs from the second starting material; and/or wherein the first starting material comprises a first vaccine and the second starting material comprises a second vaccine different from the first vaccine; and/or wherein the first starting material comprises only a first of the components *Mycoplasma* vaccine and Circovirus vaccine, preferably in amounts of more than 30% by weight, preferably more than 40% by weight, particularly more than 50% by weight; and/or less than 90% by weight, preferably less than 80% by weight, particularly less than 70% by weight; and/or wherein the second starting material comprises only the other of the components *Mycoplasma* vaccine and Circovirus vaccine; and/or wherein the second starting material comprises only one of the components *Mycoplasma* vaccine and Circovirus vaccine, preferably in amounts of more than 30% by weight, preferably more than 40% by weight, particularly more than 50% by weight; and/or less than 90% by weight, preferably less than 80% by weight, particularly less than 70% by weight; and/or wherein the first starting material, the second starting material and/or the vaccinating agent is a suspension, preferably with vaccines and/or insoluble proteins, preferably in amounts of more than 30% by weight, preferably more than 40% by weight, particularly more than 50% by weight; and/or less than 90% by weight, preferably less than 80% by weight, particularly less than 70% by weight; and/or wherein the ratio by volume of the first starting material to the second starting material is 3:1 to 1:3, preferably 2:1 to 1:2, particularly about 1:1; and/or wherein the first starting material and/or the second starting material and/or the vaccinating agent has a viscosity that is less than 10000 mPa·s, preferably less than 1000 mPa·s, particularly less than 500 mPa·s; and/or higher than 5 mPa·s, preferably higher than 10 mPa·s, particularly higher than 20 mPa·s, measured with a Brookfield viscometer according to EN ISO 2555 at 5° C.; and/or wherein the first and/or second starting material is liquid at 2° C. to 8° C.; and/or has a melting point of less than 1° C., preferably less than 0° C., particularly less than −0.2° C.; and/or higher than −1.5° C., preferably higher than −1.0° C., particularly higher than −0.8° C.; and/or wherein the vaccinating agent has a characteristic color different from the two starting materials; and/or in that the vaccinating agent has a color or no color, in contrast to at least one of the starting materials; and/or wherein mixing one of the starting materials with a third starting material that is different from the two starting materials produces no color, or a color that is different from the characteristic color of the vaccinating agent; and/or wherein the vaccinating agent is designed to prevent pigs from falling ill with *Mycoplasma* hyopneumoniae and/or Porcine Circovirus type 2; and/or wherein the *Mycoplasma* vaccine contains one or more antigens of *Mycoplasma* hyopneumoniae, preferably in amounts of more than 30% by weight, preferably more than 40% by weight, particularly more than 50% by weight; and/or less than 90% by weight, preferably less than 80% by weight, particularly less than 70% by weight; and/or wherein the Circovirus vaccine contains one or more antigens of Porcine Circovirus, preferably type 2, particularly Porcine Circovirus type 2 ORF2 protein, preferably in amounts of more than 30% by weight, preferably more than 40% by weight, particularly more than 50% by weight; and/or less than 90% by weight, preferably less than 80% by weight, particularly less than 70% by weight; and/or wherein at least one of the starting materials and/or the vaccinating agent comprises a preferably polymeric adjuvant, particularly carbomer; and/or wherein at least one of the starting materials and/or the vaccinating agent comprises the adjuvant in amounts of more than 0.1% by weight and/or less than 20% by weight, preferably more than 1% by weight and/or less than 10% by weight, particularly more than 2% by weight and/or less than 5% by weight; and/or wherein a preferably polymeric adjuvant, particularly carbomer, is formed in the vaccinating agent; and/or wherein the *Mycoplasma* vaccine and/or the Circovirus vaccine contains formaldehyde in a concentration of less than 2.5 mg/$m^3$, preferably less than 1.5 mg/$m^3$, particularly 0.74 mg/$m^3$ or less; and/or wherein the first starting material contains water in a concentration of at least 20% by weight, preferably at least 30% by weight, particularly at least 40% by weight; and/or at most 80% by weight, preferably at most 70% by weight, particularly at most 60% by weight; and/or wherein the first starting material contains one or more excipients, particularly preservatives, antioxidants and/or emulsifier, each preferably in a concentration of at least 0.1% by weight, preferably at least 0.2% by weight, particularly at least 0.3% by weight; and/or at most 10% by weight, preferably at most 5% by weight, particularly at most 3% by weight; and/or wherein the total volume of the first container exceeds the volume of the first starting material at least by the volume of the second starting material; and/or wherein the first container is filled with the first starting material in an amount of less than 70%, preferably less than 50%, particularly less than 45%; and/or wherein the first container contains gas, preferably protective gas; and/or wherein the volume of the gas corresponds at least to the volume of the second starting material in the second container; and/or wherein the volume of the gas in the first container exceeds the volume of the second starting material by more than 2%, preferably more than 5%, particularly more than 8% and/or less than 80%, preferably less than 50%, particularly less than 40% or 30%; and/or wherein the adapter device is configured so that during the transfer of the second starting material into the first container the gas or protective gas passes, particularly is transported, from the first container into the second container; and/or wherein the adapter device is configured for preferably fluidically connecting the inner spaces formed by the containers; and/or wherein the adapter device comprises a fluid channel for providing a fluidic connection between the inner spaces formed by the containers; and/or wherein the adapter device comprises a venting or exhaust device; and/or wherein the adapter device comprises a channel for venting or exhaust; and/or wherein the venting or exhaust device, particularly the channel for venting or exhaust, is provided in addition to the fluid channel of the adapter device, particularly parallel thereto; and/or wherein one opening of the channel for venting or exhaust is set back, in respect of the outlet opening of the fluid channel on the side facing the first container, in the direction of the main extent of the adapter device, and/or an opening of the channel for venting or exhaust facing the second container is arranged on the side of the outlet opening of the fluid channel facing the second container, which faces the second container, facing the open end of the adapter device; and/or wherein the venting or exhaust device is configured for in particular fluidically connecting the inner spaces formed by the containers; and/or wherein the adapter device comprises two adapter elements forming a fluid channel and/or venting or exhaust device, associated with the containers, preferably configured as a transfer needle, hollow needle and/or spike; and/or wherein between the adapter elements is provided a tube or pipe, particularly moulded thereon, preferably for extending the fluid channel; and/or wherein the adapter device is configured to be specific to the first container and/or second container; and/or wherein at least one adapter element is configured mechanically to be specific to one of the containers; and/or wherein the introduction of substances other than the first and/or second starting material into the first and/or second container is prevented; and/or wherein the adapter device is embodied to form a connection solely between the first and second container, particularly with exclusion of the surrounding atmosphere; and/or wherein the second starting material enters the first container under the effect of gravity; and/or wherein at least one of the containers, particularly the second container, is flexibly deformable; and/or wherein the first container, the second container, the closure device and/or the connecting device consists at least substantially of HDPE, EVA, halobutyl type 1 rubber and/or siliconized chlorobutyl; and/or wherein the closure device comprises or consists of a rubber stopper; and/or wherein the rubber stopper comprises or at least substantially consists of halobutyl type 1 rubber; and/or wherein for the preparation the first container, the second container and the adapter device form a sealed assembly, preferably with a common packaging; and/or wherein the vaccinating agent is intended for preventing disease in pigs caused by infection with porcine Circovirus type 2 and/or *Mycoplasma hyopneumoniae*; and/or wherein the first container can be used in or with a preferably multiple-use injection device, particularly an injection gun, pressure injector and/or self-filling syringe; and/or wherein, for use in or with a particularly multiple-use injection device, particularly an injection gun, pressure injector and/or self-filling syringe, the first container can be connected in airtight manner to a receptacle of the injection device; and/or wherein the first container is formed in a neck or mouth region, particularly by means of the closure device for connection to a particularly multiple-use injection device, particularly an injection gun, pressure injector and/or self-filling syringe; and/or wherein the longitudinal extent and/or the diameter of the first container is designed for use in a particularly multiple-use injection device, particularly an injection gun, pressure injector and/or self-filling syringe; and/or wherein the first container has a diameter of more than 1 cm, preferably more than 2 cm, particularly more than 3 cm; and/or less than 10 cm, preferably less than 8 cm, particularly less than 6 cm;

wherein the first container has a longitudinal extent that is more than 3 cm, preferably more than 5 cm, particularly more than 6 cm and/or less than 30 cm, preferably less than 25 cm, particularly less than 20 cm; and/or Process for producing and/or preparing a vaccinating agent, preferably for, in particular, simultaneous immunization against the disease Porcine Circovirus Disease "PCVD" and/or Enzootic Pneumonia "EP" by means of a kit, particularly as outlined above; or Process of vaccinating an animal or pig, applying a vaccinating agent, preferably for simultaneous immunization against two diseases, in particular Porcine Circovirus Disease "PCVD" and/or Enzootic Pneumonia "EP", preferably by means of a kit, particularly as outlined above; or Process of at least two starting materials for producing a vaccinating agent, preferably for, in particular, simultaneous immunization against the disease Porcine Circovirus Disease "PCVD" and/or Enzootic Pneumonia "EP" in pigs, in which, in order to produce the vaccinating agent, the starting materials are placed in containers and used with an adapter device, particularly using a kit as outlined above; using a first starting material in a first container only partly filled with the first starting material and a second starting material different from the first in a second container comprising the second starting material, and an adapter device designed to provide a fluidic connection between the first and second container, at least one of the containers being closed off on the operating side with a closure device and forming with the adapter device, when the closure device is pierced for the first and/or only time, a fluid connection between the first and second container, in order to transfer the second starting material through the adapter device and the closure device into the first container and produce the vaccinating agent in the first container; each of the above processes preferably comprising:

the adapter device being used to penetrate the closure device; and/or the adapter device being used to penetrate the closure devices of both containers, preferably for the first and/or only time; and/or the adapter device being used first to penetrate the closure device of the second container and then the closure device of the first container, preferably for the first and/or only time; and/or the adapter device being used to produce a fluid connection between the containers such that the starting material passes from the second container into the first container under the effect of gravity; and/or the first container being moved during and/or after the transfer of the second starting material into the first container, in order to achieve and/or speed up homogeneous mixing; and/or the first container being used with an injection device, more particularly being connected thereto; and/or the first container being used in or with a preferably multiple-use injection device, particularly an injection gun, pressure injector and/or self-filling syringe; and/or the first container being configured for use in or with a preferably multiple-use injection device, particularly an injection gun, pressure injector and/or self-filling syringe; and/or the first container being configured in a neck or mouth region for connection to a particularly multiple-use injection device, particularly an injection gun, pressure injector and/or self-filling syringe; and/or the longitudinal extent and/or diameter of the first container being designed for use in a particularly multiple-use injection device, particularly an injection gun, pressure injector and/or self-filling syringe; and/or the first container having a diameter of more than 1 cm, preferably more than 2 cm, particularly more than 3 cm and/or less than 10 cm, preferably less than 8 cm, particularly less than 6 cm; and/or the first container having a longitudinal extent which is more than 3 cm, preferably more than 5 cm, particularly more than 6 cm and/or less than 30 cm, preferably less than 25 cm, particularly less than 20 cm; and/or the first and/or second starting material being or comprising a vaccine; and/or the first starting material differing from the second starting material; and/or the first starting material comprising a first vaccine and the second starting material comprises a second vaccine that is different from the first vaccine; and/or the first starting material comprising only a first of the components *Mycoplasma* vaccine and Circovirus vaccine, preferably in amounts of more than 30% by weight, preferably more than 40% by weight, particularly more than 50% by weight; and/or less than 90% by weight, preferably less than 80% by weight, particularly less than 70% by weight; and/or the second starting material comprising only the other of the components *Mycoplasma* vaccine and Circovirus vaccine; and/or the second starting material comprising only one of the components *Mycoplasma* vaccine and Circovirus vaccine, preferably in amounts of more than 30% by weight, preferably more than 40% by weight, particularly more than 50% by weight; and/or less than 90% by weight, preferably less than 80% by weight, particularly less than 70% by weight; and/or the first starting material, the second starting material and/or the vaccinating agent being a suspension, preferably with vaccines and/or insoluble proteins, preferably in amounts of more than 30% by weight, preferably more than 40% by weight, particularly more than 50% by weight; and/or less than 90% by weight, preferably less than 80% by weight, particularly less than 70% by weight; and/or the ratio by volume of the first starting material to the second starting material being 3:1 to 1:3, preferably 2:1 to 1:2, particularly about 1:1; and/or the first starting material and/or the second starting material and/or the vaccinating agent having a viscosity which is less than 10000 mPa·s, preferably less than 1000 mPa·s, particularly less than 500 mPa·s; and/or higher than 5 mPa·s, preferably higher than 10 mPa·s, particularly higher than 20 mPa·s, measured with a Brookfield viscometer according to EN ISO 2555 at 5° C.; and/or the first and/or second starting material being liquid at 2° C. to 8° C.; and/or having a melting point of less than 1° C., preferably less than 0° C., particularly less than −0.2° C. and/or higher than −1.5° C., preferably higher than −1.0° C., particularly higher than −0.8° C.; and/or the vaccinating agent having a characteristic color different from both starting materials; and/or the vaccinating agent having a color or no color, in contrast to at least one of the starting materials; and/or mixing one of the starting materials with a third starting material different from the two starting materials producing no color or a different color from the one that is characteristic of the vaccinating agent; and/or the vaccinating agent being intended for preventing disease in pigs caused by infection with *Mycoplasma hyopneumoniae* and/or Porcine Circovirus type 2; and/or the *Mycoplasma* vaccine containing one or more antigens of *Mycoplasma hyopneumoniae*, preferably in amounts of more than 30% by weight, preferably more than 40% by weight, particularly more than 50% by weight; and/or less than 90% by weight, preferably less than 80% by weight, particularly less than 70% by weight; and/or the Circovirus vaccine containing one or more antigens of Porcine Circovirus, preferably type 2, particularly porcine Circovirus type 2 ORF2 protein, preferably in amounts of more than 30% by weight, preferably more than 40% by weight, particularly more than 50% by weight; and/or less than 90% by weight, preferably less than 80% by weight, particularly less than 70% by weight; and/or at least one of the starting materials and/or the vaccinating agent comprising a preferably polymeric adjuvant, particularly carbomer; and/or at least one of the starting materials and/or the vaccinating agent comprising the adjuvant in amounts of more than 0.1% by weight and/or less than 20% by weight, preferably more than 1% by weight and/or less than 10% by weight, particularly more than 2% by weight and/or less than 5% by weight; and/or a preferably polymeric adjuvant, particularly carbomer, being formed in the vaccinating agent; and/or the *Mycoplasma* vaccine and/or the Circovirus vaccine containing formaldehyde in a concentration of less than 2.5 mg/m³, preferably less than 1.5 mg/m³, particularly 0.74 mg/m³ or less; and/or the first starting material containing water in a concentration of at least 20% by weight, preferably at least 30% by weight, particularly at least 40% by weight; and/or at most 80% by weight, preferably at most 70% by weight, particularly at most 60% by weight; and/or the first starting material containing one or more excipients, particularly preservatives, antioxidants and/or emulsifier, each preferably in a concentration of at least 0.1% by weight, preferably at least 0.2% by weight, particularly at least 0.3% by weight; and/or at most 10% by weight, preferably at most 5% by weight, particularly at most 3% by weight; and/or the total volume of the first container exceeding the volume of the first starting material at least by the volume of the second starting material; and/or the first container being filled with the first starting material by an amount of less than 70%, preferably less than 50%, particularly less than 45%; and/or the first container containing gas, preferably protective gas; and/or the volume of the gas corresponding at least to the volume of the second starting material in the second container; and/or the volume of the gas in the first container exceeding the volume of the second starting material by more than 2%, preferably more than 5%, particularly more than 8% and/or less than 80%, preferably less than 50%, particularly less than 40% or 30%; and/or the adapter device being configured so that, during the transfer of the second starting material into the first container, the gas or protective gas passes, particularly is transported, from the first container into the second container; and/or the adapter device being configured for preferably fluidically connecting the inner spaces formed by the containers; and/or the adapter device comprising a fluid channel for providing a fluidic connection between the inner spaces formed by the containers; and/or the adapter device comprising a venting or exhaust device; and/or the adapter device comprising a channel for venting or exhaust; and/or the venting or exhaust device, particularly the channel for venting or exhaust, being provided in addition to the fluid channel of the adapter device, particularly parallel thereto; and/or an opening of the channel for venting or exhaust being set back, in respect of the outlet opening of the fluid channel on the side facing the first container, in the direction of the main extent of the adapter device; and/or the venting or exhaust device being configured for, in particular, fluidically connecting the inner spaces formed by the containers; and/or the adapter device comprising two adapter elements forming a fluid channel and/or venting or exhaust device, associated with the containers, preferably configured as a transfer needle, hollow needle and/or spike; and/or a tube or pipe being provided between the adapter elements, particularly molded thereon, preferably for extending the fluid channel; and/or the adapter device, particularly an adapter element, being configured to be specific to the first container and/or second container; and/or at least one adapter element being configured mechanically to be specific to one of the containers; and/or the introduction of substances other than the first and/or second starting material into the first and/or second container being prevented; and/or the adapter device being embodied to form a connection solely between the containers, particularly with exclusion of the surrounding atmosphere; and/or being the second starting material entering the first container under the effect of gravity; and/or at least one of the containers, particularly the second container, being flexibly deformable; and/or the first container, the second container, the closure device and/or the connecting device being made at least substantially of HDPE, EVA, halobutyl type 1 rubber and/or siliconised chlorobutyl; and/or the closure device comprising a rubber stopper; and/or the rubber stopper being least substantially made of halobutyl type 1 rubber; and/or for the preparation the first container, the second container and the adapter device forming a sealed assembly, preferably with a common packaging; and/or the vaccinating agent being intended for preventing disease in pigs caused by infection with porcine Circovirus type 2 and/or *Mycoplasma hyopneumoniae*.

What is claimed is:

1. Kit for preparing a vaccinating agent, for immunization against at least one of Porcine Circovirus Disease "PCVD" and Enzootic Pneumonia "EP", the kit comprising:
   a first starting material,
   a second starting material different from the first starting material, the first and second starting materials being materials that result in the vaccinating agent when combined,
   a first container only partially filled with a volume of the first starting material,
   a second container containing a volume of the second starting material and
   an adapter device comprising a pair of oppositely facing piercing elements in the form of conical spikes for providing a fluid connection between the first and second containers,
      wherein at least one of the containers is closed off with a factory-provided closure device,
      wherein the second container is connectable to the first container with the adapter device by piercing the closure device in a manner enabling the second starting material to enter the first container to form the vaccinating agent therein with the first starting material,
      wherein the first starting material is liquid,
      wherein the second starting material is liquid,
      wherein the second container is filled with said volume of the second starting material,
      wherein, for the homogeneous preparation of the vaccinating agent in the first container, the first container has a total volume that exceeds the volume of the first starting material by at least the volume of the second material, and
      wherein the adapter has a first through channel for the passage of the liquid second starting material into the first container and a second through channel for the passage of gas from the first container into the second container, an end of the second through passage facing the first container being disposed further from a pointed end of the conical spike of a respective one of the piercing elements than the opening of the first channel inserted into the first container and an opposite end of the second through channel being disposed closer to a pointed end of the conical spike of the opposite one of the piercing elements than an opposite end of the opening of the first channel inserted into the second container.

2. Kit according to claim 1, wherein the first starting material comprises a first vaccine and the second starting material comprises a second vaccine different from the first vaccine.

3. Kit according to claim 1, wherein the first starting material comprises only one of *Mycoplasma* vaccine and Circovirus vaccine.

4. Kit according to claim 3, wherein the second starting material comprises only the remaining component of the *Mycoplasma* vaccine and Circovirus vaccine.

5. Kit according to claim 1, wherein the first starting material comprises *Mycoplasma* vaccine in amounts of more than 30% by weight and the second starting material comprises Circovirus vaccine in amounts of more than 30% by weight.

6. Kit according to claim 1, wherein the vaccinating agent has a characteristic color different from that of the starting materials.

7. Kit according to claim 1, wherein the vaccinating agent is an agent for preventing animals from falling ill.

8. Kit according to claim 1, wherein at least one of the starting materials and the vaccinating agent comprises an adjuvant.

9. Kit according to claim 8, wherein the adjuvant is polymeric.

10. Kit according to claim 1, wherein at least the second container is flexibly deformable.

11. Kit according to claim 1, wherein the first container is filled with the first starting material in an amount of less than 70%.

12. Kit according to claim 1, wherein the ratio by volume of the first starting material to the second starting material is 3:1 to 1:3.

13. Kit according to claim 1, wherein the first and/or second starting material is liquid at 2° C. to 8° C. or has a melting point of less than 1° C.

14. Kit according to claim 1, wherein the second starting material enters the first container under the effect of gravity.

15. Kit according to claim 1, wherein the first container contains protective gas.

* * * * *